(12) United States Patent
Cote

(10) Patent No.: US 12,153,034 B2
(45) Date of Patent: Nov. 26, 2024

(54) CARBON MONOXIDE DETECTING ELECTRICAL RECEPTACLE ASSEMBLY

(71) Applicant: John Cote, Rowlett, TX (US)

(72) Inventor: John Cote, Rowlett, TX (US)

( * ) Notice: Subject to any disclaimer, the term of this patent is extended or adjusted under 35 U.S.C. 154(b) by 30 days.

(21) Appl. No.: 18/133,162

(22) Filed: Apr. 11, 2023

(65) Prior Publication Data

US 2024/0345051 A1    Oct. 17, 2024

(51) Int. Cl.
*G01N 33/00* (2006.01)
*G08B 21/18* (2006.01)

(52) U.S. Cl.
CPC ....... *G01N 33/0063* (2013.01); *G08B 21/182* (2013.01)

(58) Field of Classification Search
CPC .................................................. G01N 33/0063
See application file for complete search history.

(56) References Cited

U.S. PATENT DOCUMENTS

| | | | |
|---|---|---|---|
| 5,201,879 A * | 4/1993 | Steele | F24F 13/08 454/283 |
| 7,515,058 B2 | 4/2009 | Normand | |
| 8,857,463 B1 * | 10/2014 | Carruth | G01N 33/004 137/514.7 |
| 9,444,244 B2 | 9/2016 | Hooper | |
| 9,600,998 B2 | 3/2017 | Mumey | |
| D945,370 S | 3/2022 | Chen | |
| 11,632,526 B2 * | 4/2023 | Ogino | H04N 9/3152 353/38 |
| 2018/0182218 A1 | 6/2018 | Toland | |
| 2018/0248389 A1 * | 8/2018 | Toya | H01M 50/204 |
| 2020/0348639 A1 | 11/2020 | Alexander | |
| 2021/0132021 A1 * | 5/2021 | Brown | G01N 33/0063 |
| 2022/0212522 A1 * | 7/2022 | Skipton | B01D 46/0008 |
| 2022/0351595 A1 * | 11/2022 | Ryznic | G08B 19/00 |

FOREIGN PATENT DOCUMENTS

CA    3080020    11/2020

OTHER PUBLICATIONS

Andy, Nov. 24, 2021, What is Type B Power Plug and Socket (Outlet) pp. 1, 3, and 4, 2021.*

* cited by examiner

*Primary Examiner* — Nabil H Syed
*Assistant Examiner* — Cal J Eustaquio

(57) ABSTRACT

A carbon monoxide detecting electrical receptacle assembly for alerting a user to dangerous levels of carbon monoxide includes a housing that is attachable to an electrical box. A socket in a front face of the housing allows for insertion of a corresponding plug. A set of connectors attached to electrical wiring operationally engages the socket, a sensor, a notification module, and an indicator light to an electrical circuit. The sensor measures a level of carbon monoxide in air proximate to the housing. The notification module notifies a user when the level of carbon monoxide reaches a preset value. The indicator light selectively emits a first color of light and a second color of light when the level of carbon dioxide is below and equal to or greater than the preset value, respectively.

11 Claims, 5 Drawing Sheets

CARBON MONOXIDE DETECTING ELECTRICAL RECEPTACLE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to electrical receptacles and more particularly pertains to a new electrical receptacle for alerting a user to dangerous levels of carbon monoxide. The present invention discloses an electrical receptacle having a socket, a sensor that measures a level of carbon monoxide, and a notification module that notifies a user when the level of carbon monoxide reaches a preset value.

(2) Description of Related Art Including Information Disclosed Under 37 CFR 1.97 and 1.98

The prior art relates to electrical receptacles, which may comprise extension cords, or the like, with integral carbon monoxide sensors, electrical box mountable carbon monoxide sensor and outlet combinations that protrude from the electrical boxes, and electrical receptacles having carbon monoxide sensor in communicative engagement with other devices, such as smoke alarms, security systems, and phones. What is lacking in the prior art is an electrical receptacle comprising a housing sized complementarily to and attachable within an electrical box. The electrical receptacle comprises a socket, a sensor, a notification module, and an indicator light. The sensor measures carbon monoxide and the notification notifies a user when the level of carbon monoxide reaches a preset value, concurrently with the indicator light emitting red light.

BRIEF SUMMARY OF THE INVENTION

An embodiment of the disclosure meets the needs presented above by generally comprising a housing, which defines an interior space. A set of holed tabs is attached to and extends from the housing so that the housing is configured for attachment to an electrical box. A socket is positioned in a front face of the housing and is configured for insertion of a corresponding plug. A set of connectors is attached to the housing and is operationally engaged to the socket. The connectors are configured to be connected to electrical wiring to operationally engage the socket to an electrical circuit.

A sensor is attached to the housing, is positioned in the interior space, is operationally engaged to the set of connectors, and is configured to measure a level of carbon monoxide in air proximate to the housing. A notification module is attached to the housing and is operationally engaged to the sensor and to the set of connectors. The notification module is configured to notify a user when the level of carbon monoxide reaches a preset value. An indicator light is attached to the front face of the housing and is operationally engaged to the sensor and to the set of connectors. The indicator light is configured to selectively emit a first color of light and a second color of light when the level of carbon dioxide is below and equal to or greater than the preset value, respectively.

Another embodiment of the disclosure includes a carbon monoxide detecting electrical receptacle system, which comprises a carbon monoxide detecting electrical receptacle, as described in the disclosure above, an electrical box, from which extends electrical wiring that is integral to an electrical circuit. The electrical box is mounted to an element of a structure and the housing is mounted to the electrical box. A socket, a sensor, and a notification module are operationally engaged to the electrical wiring by a set of connectors. The notification module is configured to notify a user when the level of carbon monoxide reaches a preset value. The indicator light is configured to selectively emit a first color of light and a second color of light when the level of carbon dioxide is less than and equal to or greater than the preset value, respectively.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
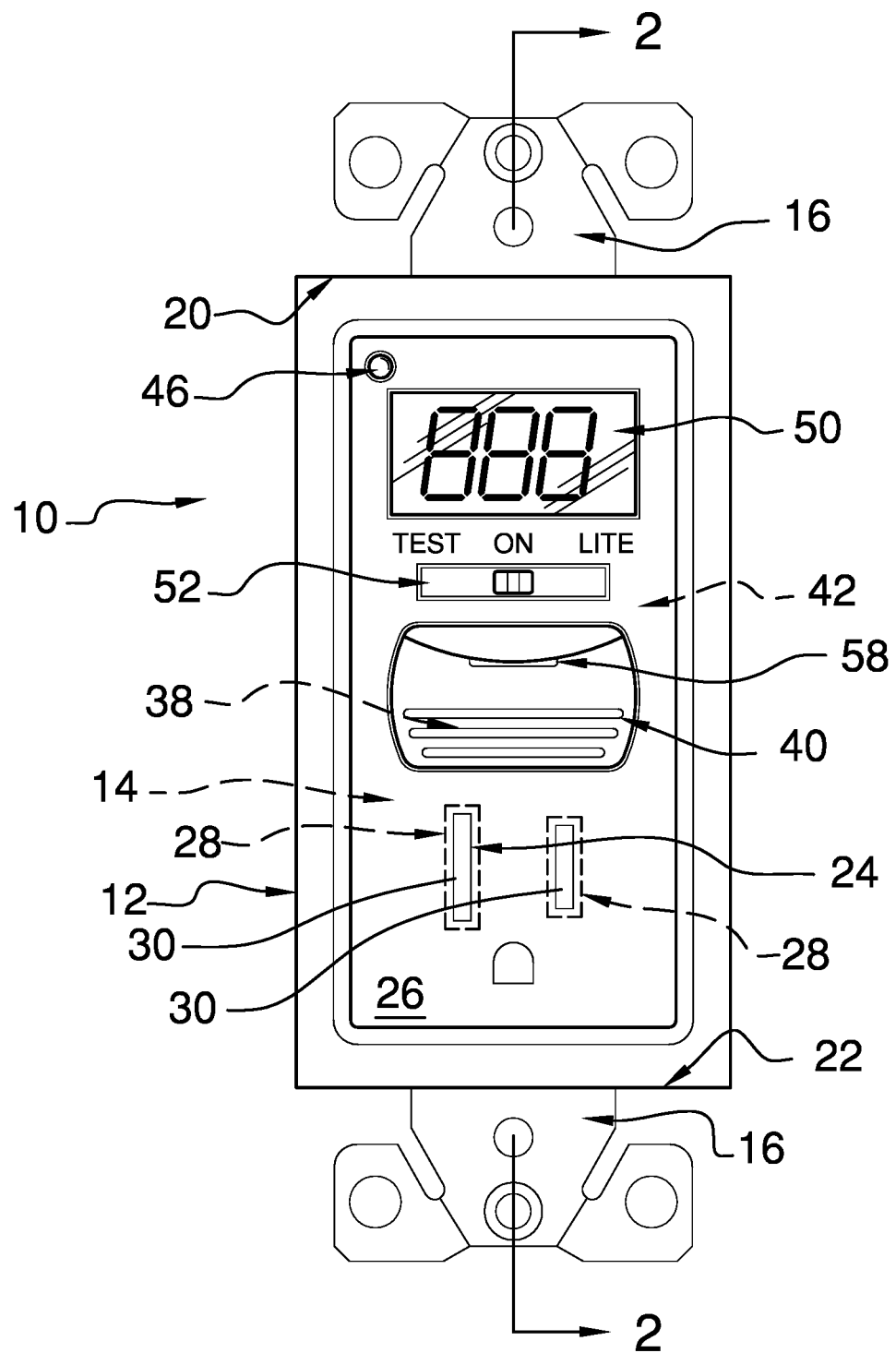
FIG. 1 is a front view of a carbon monoxide detecting electrical receptacle assembly according to an embodiment of the disclosure.
Figure 2:
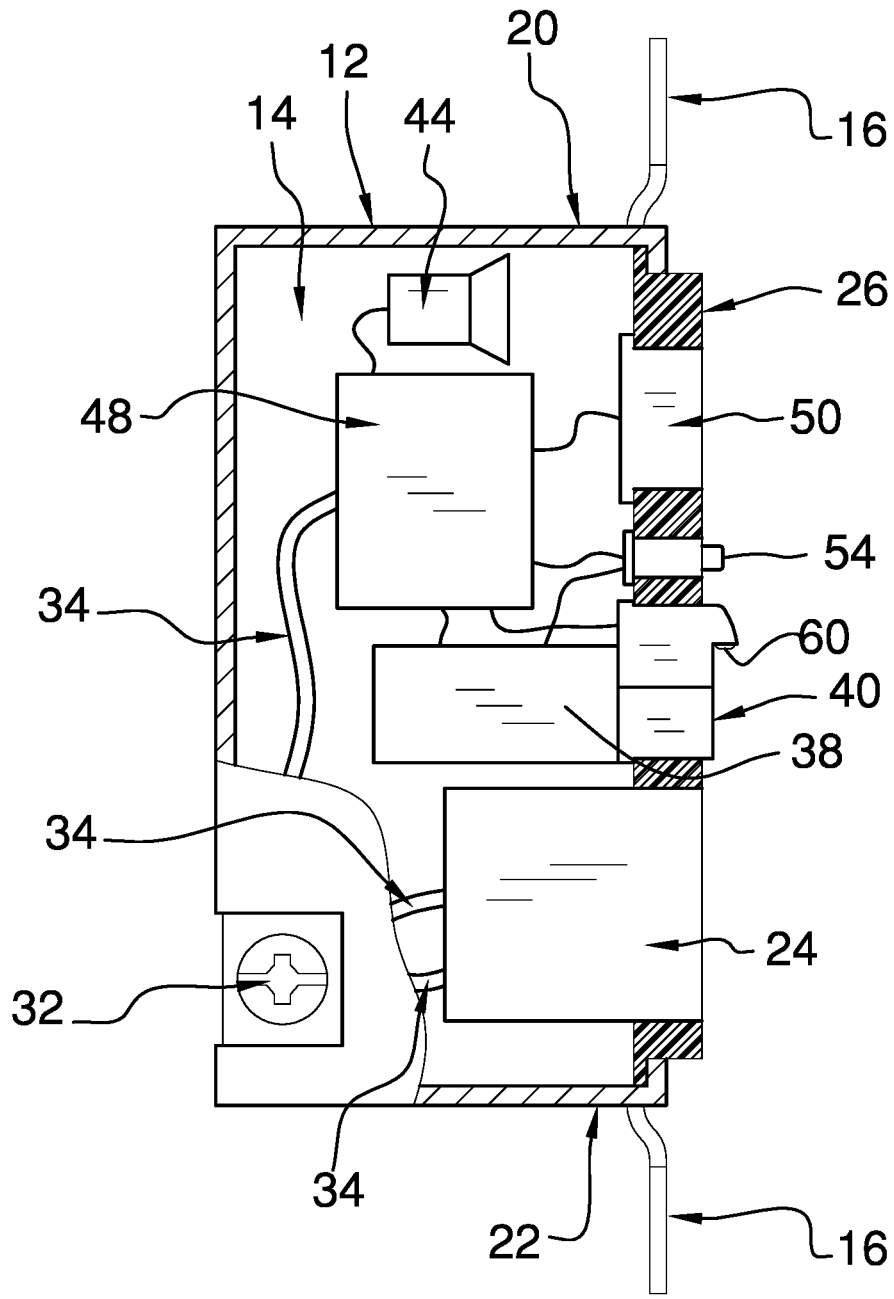
FIG. 2 is a cross-sectional view of an embodiment of the disclosure.

With reference now to the drawings, and in particular to FIGS. 1 through 5 thereof, a new electrical receptacle embodying the principles and concepts of an embodiment of the disclosure and generally designated by the reference numeral 10 will be described.

As best illustrated in FIGS. 1 through 5, the carbon monoxide detecting electrical receptacle assembly 10 generally comprises a housing 12, which is cuboid and which defines an interior space 14. A set of holed tabs 16 is attached to and extends from the housing 12 so that the housing 12 is configured for attachment to an electrical box 18. As shown in FIG. 1, the set of holed tabs 16 comprises two holed tabs 16 extending singly from a top 20 and a bottom 22 of the housing 12, which is a typical arrangement for attaching elements to an electrical box 18.

A socket 24 is positioned in a front face 26 of the housing 12 and is configured for insertion of a corresponding plug (not shown). As shown in FIG. 1, the socket 24 comprises a National Electrical Manufacturers Association (NEMA) Type B socket. The present invention anticipates the socket 24 comprising other types of NEMA sockets, or sockets utilized in geographic locations outside of North America. The present invention also anticipates the carbon monoxide detecting electrical receptacle assembly 10 comprising one or more Universal Serial Bus ports (not shown) and being configured for Ground Fault Circuit Interruption.

A pair of shutters 28 may be attached to the housing 12 so that each shutter 28 extends across a respective slot 30 of a pair of slots 30 of the socket 24. The pair of shutters 28 is spring loaded and is configured to deter tampering with the socket 24. Such tamper resistant means are well known to those skilled in the art of sockets.

A set of connectors 32 is attached to the housing 12 and is operationally engaged to the socket 24. The connectors 32 are configured to be connected to electrical wiring 34 to operationally engage the socket 24 to an electrical circuit 36. A variety of connecting means for connecting receptacles to wiring, such as, but not limited to, screws, push in wire connectors, and the like, are known in the prior art and these are all anticipated by the present invention.

A sensor 38 is attached to the housing 12, is positioned in the interior space 14, is operationally engaged to the set of connectors 32, and is configured to measure a level of carbon monoxide in air proximate to the housing 12. A plurality of slits 40 is positioned in the front face 26 of the housing 12 proximate to the sensor 38 and is configured to allow entry of the air into the sensor 38 so that the sensor 38 is enabled to measure the carbon monoxide level of the air.

A notification module 42 is attached to the housing 12 and is operationally engaged to the sensor 38 and to the set of connectors 32. The notification module 42 may comprise a speaker 44, which is configured to emit an audio signal when the level of carbon monoxide reaches the preset value, or other notification means, such as a bright flashing or strobing light, which would be beneficial to a user who is deaf or hard of hearing. The notification module 42 is configured to notify a user when the level of carbon monoxide reaches a preset value.

An indicator light 46 is attached to the front face 26 of the housing 12 and is operationally engaged to the sensor 38 and to the set of connectors 32. The indicator light 46 is configured to selectively emit a first color of light and a second color of light when the level of carbon dioxide is below and equal to or greater than the preset value, respectively. The indicator light 46 emits green light when the level of carbon dioxide is less than the preset value. The indicator light 46 emits red light when the level of carbon dioxide is equal to or greater than the preset value. The indicator light 46 also may be configured to selectively emit a third color of light, such as yellow light, when the sensor 38 is malfunctioning.

A microprocessor 48 is attached to the housing 12, is positioned in the interior space 14, and is operationally engaged to the sensor 38, the notification module 42, the indicator light 46, and the set of connectors 32. The microprocessor 48 is enabled to monitor the level of carbon monoxide and to selectively actuate the notification module 42 and the indicator light 46 to notify the user when the level of carbon monoxide reaches the preset value.

The present invention also anticipates a bulb 58 attached to the front face 26 of the housing 12, operationally engaged to the microprocessor 48, and configured to selectively illuminate an area proximate to the housing 12. The bulb 58 may comprise a light emitting diode 50, an incandescent bulb, or the like. The present invention also anticipates the carbon monoxide detecting electrical receptacle assembly 10 comprising a photosensor (not shown), which would be attached to the front face 26 of the housing 12 and which would be operationally engaged to the microprocessor 48. The photosensor would measure ambient light proximate to the housing 12 and would signal the microprocessor 48, enabling the microprocessor 48 to selectively actuate the bulb 58 under low ambient light conditions.

A display screen 50 is attached to the front face 26 of the housing 12 and is operationally engaged to the microprocessor 48. The microprocessor 48 is enabled to selectively actuate the display screen 50 to present a visual readout of the level of carbon monoxide. The present invention also anticipates the microprocessor 48 selectively actuating the display screen 50 to read END, concurrently with the indicator light 46 displaying yellow, to indicate the sensor 38 is no longer operational.

As shown in FIG. 1, a controller 52 is attached to the front face 26 of the housing 12 and is operationally engaged to the microprocessor 48. The controller 52 is configured to be manipulated by the user to signal the microprocessor 48 to selectively actuate the bulb 58, to selectively actuate the display screen 50, and to selectively test the sensor 38. The controller 52 may comprise a slide switch 54, as shown in FIG. 1, or other controlling means, such as, but not limited to, dials, touch displays, or the like. The slide switch 54 has three positions and is spring loaded so that the slide switch 54 is biased to a central position, as is shown in FIG. 1.

The slide switch 54 is configured to be slid to the right a first time to actuate the bulb 58 and to be slid to the right a second time to deactuate the bulb 58. The present invention also anticipates the bulb 58 being configured to selectively emit white and blue light. The color of the light would be selectable by sliding the slide switch 54 to the right and holding for a first prescribed time for white light and a second prescribed time for blue light. The slide switch 54 also is configured to be slid and held to the left for a prescribed time (such as three seconds) to actuate the speaker 44 and the display screen 50.

Figure 3:
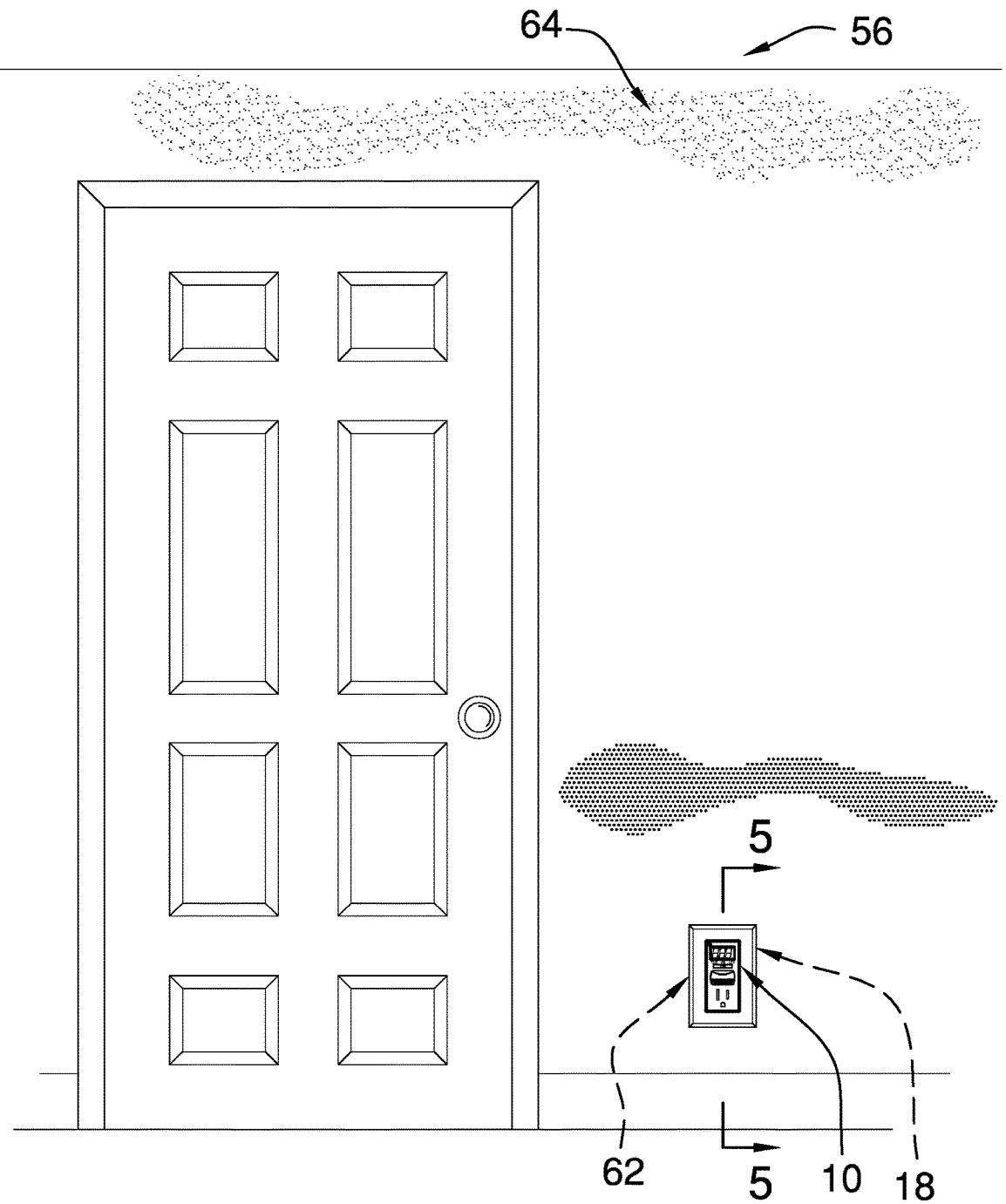
FIG. 3 is an in-use view of an embodiment of the disclosure.
Figure 4:
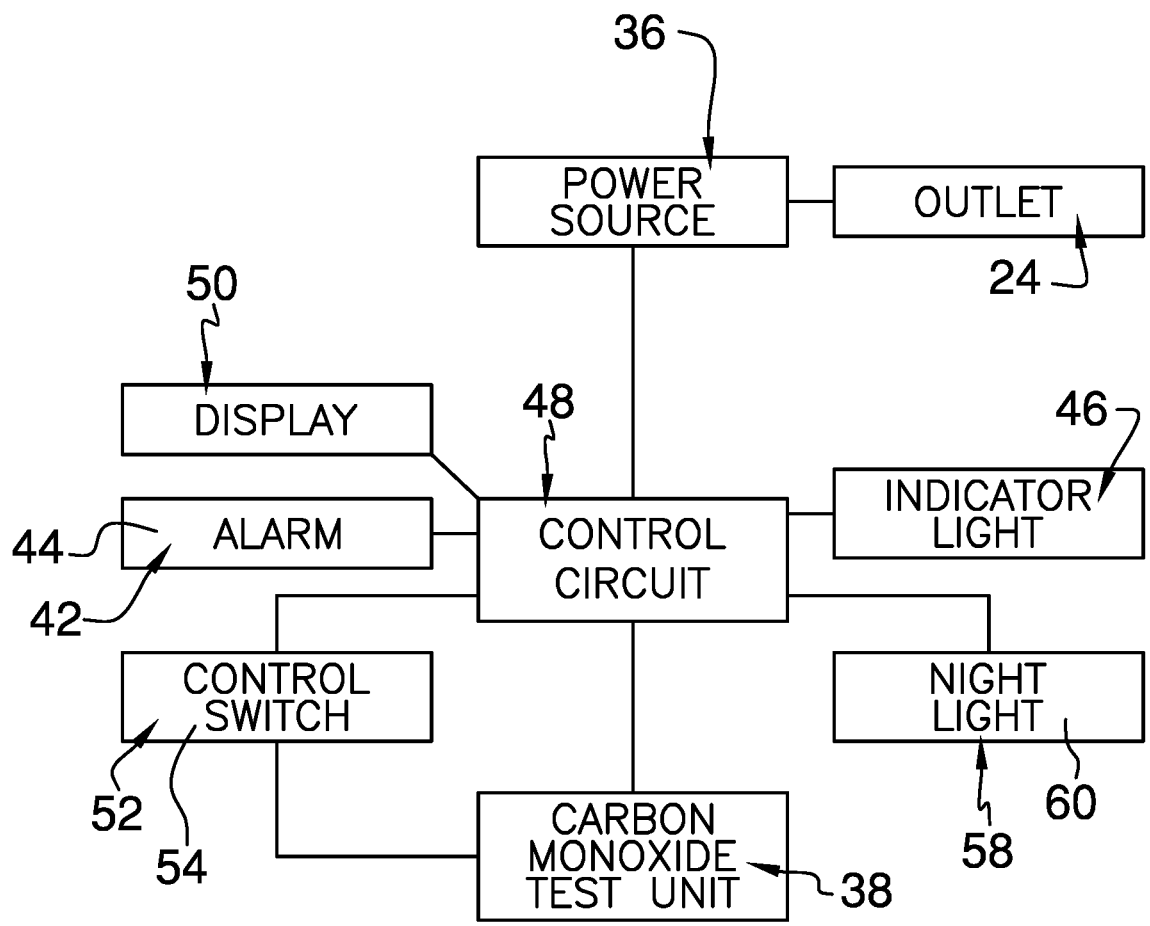
FIG. 4 is a block diagram of an embodiment of the disclosure.
Figure 5:
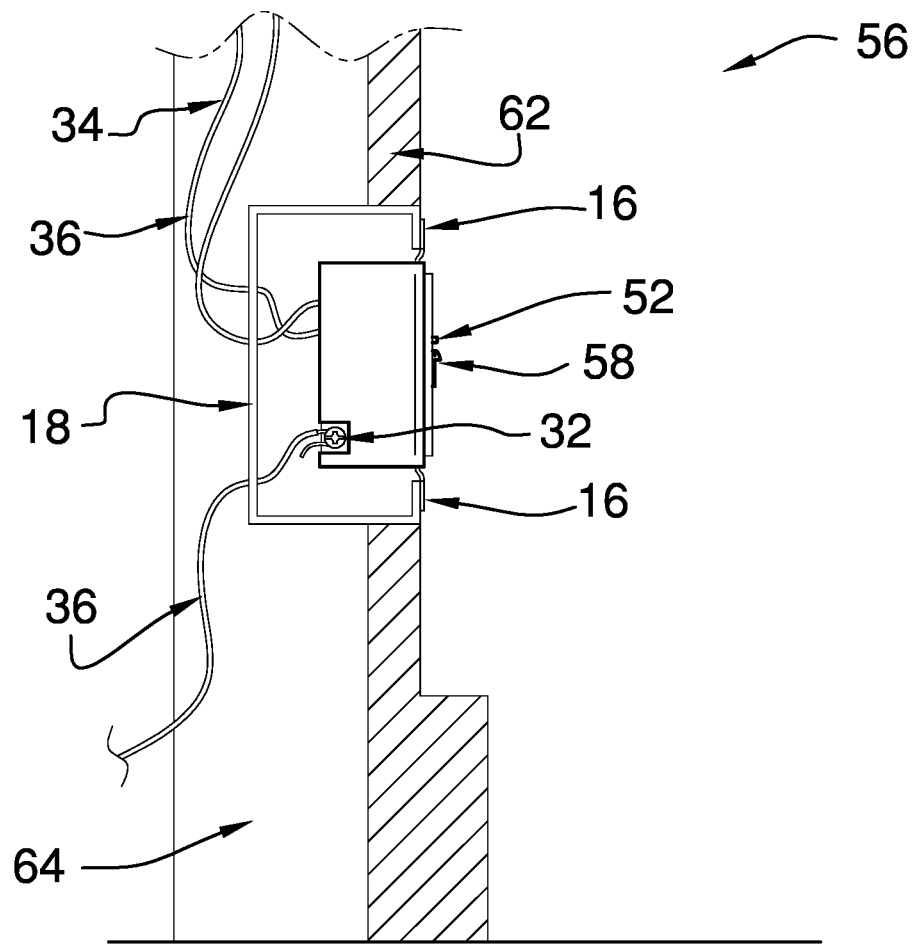
FIG. 5 is a cross-sectional in-use view of an embodiment of the disclosure.

The present invention anticipates a carbon monoxide detecting electrical receptacle system 56, as shown in FIGS. 3 and 5. The carbon monoxide detecting electrical receptacle system 56 comprises a carbon monoxide detecting electrical receptacle, as described in the specification above, and an electrical box 18, from which extends electrical wiring 34 that is integral to an electrical circuit 36. The electrical box 18 is mounted to an element 62 of a structure 64 and the housing 12 is mounted to the electrical box 18. A socket 24, a sensor 38, and a notification module 42 are operationally engaged to the electrical wiring 34 by a set of connectors 32. The notification module 42 is configured to notify a user when the level of carbon monoxide reaches a preset value. The indicator light 46 is configured to selectively emit a first color of light and a second color of light when the level of carbon dioxide is less than and equal to or greater than the preset value, respectively.

In use, the carbon monoxide detecting electrical receptacle assembly 10 is connected to an electrical circuit 36 and mounted within an electrical box 18. Should the sensor 38 detect dangerous carbon monoxide levels, the speaker 44 is actuated to alert the user. The indicator light 46 also turns red under these conditions. The carbon monoxide detecting electrical receptacle assembly 10 also includes a bulb 58 to selectively illuminate an area proximate to the housing 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A carbon monoxide detecting electrical receptacle assembly comprising:
    a housing defining an interior space;
    a set of holed tabs attached to and extending from the housing, wherein the housing is configured for attachment to an electrical box;
    a socket positioned in a front face of the housing and being configured for insertion of a corresponding plug;
    a set of connectors attached to the housing and operationally engaged to the socket, wherein the connectors of the set of connectors are configured for connecting to electrical wiring for operationally engaging the socket to an electrical circuit;
    a sensor attached to the housing, positioned in the interior space, operationally engaged to the set of connectors, and configured for measuring a level of carbon monoxide in air proximate to the housing;
    a notification module attached to the housing and operationally engaged to the sensor and the set of connectors, wherein the notification module is configured for notifying a user when the level of carbon monoxide reaches a preset value;
    an indicator light attached to the front face of the housing and operationally engaged to the sensor and the set of connectors, the indicator light being configured for selectively emitting a first color of light and a second color of light when the level of carbon dioxide is below and equal to or greater than the preset value, respectively;
    a microprocessor attached to the housing, positioned in the interior space, and being operationally engaged to the sensor, the notification module, the indicator light, and the set of connectors, such that the microprocessor is enabled for monitoring the level of carbon monoxide and for selectively actuating the notification module and the indicator light for notifying the user when the level of carbon monoxide reaches the preset value;
    a bulb attached to the front face of the housing, operationally engaged to the microprocessor, and being configured for selectively illuminating an area proximate to the housing;
    a display screen attached to the front face of the housing and operationally engaged to the microprocessor, such that the microprocessor is enabled for selectively actuating the display screen for presenting visual readout of the level of carbon monoxide; and
    a controller attached to the front face of the housing and operationally engaged to the microprocessor, wherein the controller is configured for being manipulated by the user for signaling the microprocessor for selectively actuating the bulb, for selectively actuating the display screen, and for selectively testing the sensor, wherein the controller comprising a slide switch having three positions, the slide switch being spring loaded, such that the slide switch is biased to a central position, wherein the slide switch is configured for being slid to the right a first time for actuating the bulb and for being slid to the right a second time for deactuating the bulb, and wherein the slide switch is configured for being slid and held to the left for a prescribed time for actuating the speaker and the display screen.

2. The carbon monoxide detecting electrical receptacle assembly of claim 1, wherein;
    the housing is cuboid; and
    the set of holed tabs comprises two holed tabs extending singly from a top and a bottom of the housing.

3. The carbon monoxide detecting electrical receptacle assembly of claim 1, wherein the socket comprises a National Electrical Manufacturers Association Type B socket.

4. The carbon monoxide detecting electrical receptacle assembly of claim 1, further including a pair of shutters attached to the housing such that each shutter of the pair of shutters extends across a respective slot of a pair of slots of the socket, the pair of shutters being spring loaded, wherein the pair of shutters is configured for deterring tampering with the socket.

5. The carbon monoxide detecting electrical receptacle assembly of claim 1, further including a plurality of slits positioned in the front face of the housing proximate to the sensor, wherein the plurality of slits is configured for entry of the air into the sensor, such that the sensor is enabled for measuring the carbon monoxide level of the air.

6. The carbon monoxide detecting electrical receptacle assembly of claim 1, wherein the notification module comprises a speaker configured for emitting an audio signal when the level of carbon monoxide reaches the preset value.

7. The carbon monoxide detecting electrical receptacle assembly of claim 1, wherein;

the indicator light emits green light when the level of carbon dioxide is less than the preset value; and the indicator light emits red light when the level of carbon dioxide is equal to or greater than the preset value.

8. The carbon monoxide detecting electrical receptacle assembly of claim 1, wherein the indicator light is configured for selectively emitting a third color of light when the sensor is malfunctioning.

9. The carbon monoxide detecting electrical receptacle assembly of claim 8, wherein the indicator light is configured for selectively emitting yellow light when the sensor is malfunctioning.

10. The carbon monoxide detecting electrical receptacle assembly of claim 1, wherein the bulb comprises a light emitting diode.

11. A carbon monoxide detecting electrical receptacle assembly comprising:
- a housing defining an interior space, the housing being cuboid;
- a set of holed tabs attached to and extending from the housing, wherein the housing is configured for attachment to an electrical box, the set of holed tabs comprising two holed tabs extending singly from a top and a bottom of the housing;
- a socket positioned in a front face of the housing and being configured for insertion of a corresponding plug, the socket comprising a National Electrical Manufacturers Association Type B socket;
- a pair of shutters attached to the housing such that each shutter of the pair of shutters extends across a respective slot of a pair of slots of the socket, the pair of shutters being spring loaded, wherein the pair of shutters is configured for deterring tampering with the socket;
- a set of connectors attached to the housing and operationally engaged to the socket, wherein the connectors of the set of connectors are configured for connecting to electrical wiring for operationally engaging the socket to an electrical circuit;
- a sensor attached to the housing, positioned in the interior space, operationally engaged to the set of connectors, and configured for measuring a level of carbon monoxide in air proximate to the housing;
- a plurality of slits positioned in the front face of the housing proximate to the sensor, wherein the plurality of slits is configured for entry of the air into the sensor, such that the sensor is enabled for measuring the carbon monoxide level of the air;
- a notification module attached to the housing and operationally engaged to the sensor and the set of connectors, wherein the notification module is configured for notifying a user when the level of carbon monoxide reaches a preset value, the notification module comprising a speaker configured for emitting an audio signal when the level of carbon monoxide reaches the preset value;
- an indicator light attached to the front face of the housing and operationally engaged to the sensor and the set of connectors, the indicator light being configured for selectively emitting a first color of light and a second color of light when the level of carbon dioxide is less than and equal to or greater than the preset value, respectively, the indicator light emitting green light when the level of carbon dioxide is less than the preset value, the indicator light emitting red light when the level of carbon dioxide is equal to or greater than the preset value, the indicator light being configured for selectively emitting a third color of light when the sensor is malfunctioning, the indicator light being configured for selectively emitting yellow light when the sensor is malfunctioning;
- a microprocessor attached to the housing, positioned in the interior space, and being operationally engaged to the sensor, the notification module, the indicator light, and the set of connectors, such that the microprocessor is enabled for monitoring the level of carbon monoxide and for selectively actuating the notification module and the indicator light for notifying the user when the level of carbon monoxide reaches the preset value;
- a bulb attached to the front face of the housing, operationally engaged to the microprocessor, and being configured for selectively illuminating an area proximate to the housing, the bulb comprising a light emitting diode;
- a display screen attached to the front face of the housing and operationally engaged to the microprocessor, such that the microprocessor is enabled for selectively actuating the display screen for presenting visual readout of the level of carbon monoxide; and
- a controller attached to the front face of the housing and operationally engaged to the microprocessor, wherein the controller is configured for being manipulated by the user for signaling the microprocessor for selectively actuating the bulb, for selectively actuating the display screen, and for selectively testing the sensor, the controller comprising a slide switch having three positions, the slide switch being spring loaded, such that the slide switch is biased to a central position, wherein the slide switch is configured for being slid to the right a first time for actuating the bulb and for being slid to the right a second time for deactuating the bulb, and wherein the slide switch is configured for being slid and held to the left for a prescribed time for actuating the speaker and the display screen.

* * * * *